(12) United States Patent
Glanzmann et al.

(10) Patent No.: US 8,492,578 B2
(45) Date of Patent: Jul. 23, 2013

(54) COMPOUNDS USEFUL IN THERAPEUTIC AND COSMETIC METHODS

(75) Inventors: Thomas Glanzmann, Lausanne (CH); Jérôme Barge, Romanel-sur-Lausanne (CH); Georges Wagnieres, Lutry (CH)

(73) Assignee: Photoderma SA, Ecublens (CH)

( * ) Notice: Subject to any disclaimer, the term of this patent is extended or adjusted under 35 U.S.C. 154(b) by 373 days.

(21) Appl. No.: 12/735,214

(22) PCT Filed: Dec. 12, 2008

(86) PCT No.: PCT/IB2008/055272
§ 371 (c)(1),
(2), (4) Date: Jun. 17, 2010

(87) PCT Pub. No.: WO2009/077960
PCT Pub. Date: Jun. 25, 2009

(65) Prior Publication Data
US 2010/0273725 A1    Oct. 28, 2010

(30) Foreign Application Priority Data

Dec. 14, 2007  (EP) .................................... 07123268
Jul. 4, 2008    (CH) .................................... 1040/08

(51) Int. Cl.
*C07C 229/00* (2006.01)
(52) U.S. Cl.
USPC ........................................................ 560/155
(58) Field of Classification Search
None
See application file for complete search history.

(56) References Cited

U.S. PATENT DOCUMENTS

| 6,034,267 A | 3/2000 | Gierskcky et al. |
| 2006/0084701 A1 | 4/2006 | Gierskeky et al. |

FOREIGN PATENT DOCUMENTS

| WO | WO 03/041673 | 5/2003 |
| WO | WO 03/086460 | 10/2003 |
| WO | WO 2006/051269 | 5/2006 |
| WO | WO 2008/106966 | 9/2008 |

OTHER PUBLICATIONS

Berger et al., Journal of Medicinal Chemistry, 2000, vol. 43, No. 25.*

(Continued)

*Primary Examiner* — Karl J Puttlitz
(74) *Attorney, Agent, or Firm* — Krieg DeVault LLP; Clifford W. Browning

(57) ABSTRACT

The present invention relates to photosensitizer compounds for use in cosmetic and therapeutic applications of photodynamic therapy. The compounds of the present invention are designed for topical application and are characterized by a low permeability to the stratum corneum (the outer skin layer of an individual) and/or a low allergenic potential. Surprisingly, such compounds have beneficial properties in the treatment of certain diseases and lack the undesired damages to healthy skin entailed by prior art compounds. ALA (5-aminolevulinic acid)-esters of body-owned, natural compound such as aminoacids, steroids, carbohydrates, alcohols are preferred examples of photosensitizers of the present invention. The compounds of the present invention are used in the treatment of skin diseases such as psoriasis, sebaceous glands related conditions including acne, seborrhoic dermatitis, rosacea, skin cancer and precancer, as well as in cosmetic hair removal.

5 Claims, 9 Drawing Sheets

OTHER PUBLICATIONS

Database Caplus Chemical Abstracts Service, Columbus, Ohio, US; Database Accession No. 2003:917072, Abstract of Brunner et al., Photochemistry and Photobiology (2003), 78(5), 481-486.*

Matthew J. Harris et al.; Allergic contact dermatitis to methyl aminolevulinate (Metvix) cream used in photodynamic therapy; The Dermatology Centre, Journal compilation 2007, Photodermatol Photoimmunol Photomed 2007; 23: 35-36.

Jungersted, J.M. et al.; Allergic reactions to Metvix (ALA-ME); Contact Dermatitis 2008: 58: 184-186.

Database WPI Week 200280; Thomson Scientific, London, GB, AN 1996433721, XP002525946 & RU 2 191 010 CS; Oct. 20, 2002; Abstract.

Berger Y. et al.; Ethylene Glycol and Amino Acid Derivatives of 5-Aminolevulinic Acid As New Photosensitizing Percursors of Protoporphyrin Ix in Cells; Dec. 1, 2000; Journal of Medicinal Chemistry, American Chemical Society, pp. 4738-4746.

Metvix Package leaflet: information for the user; Jan. 16, 2008.

* cited by examiner

US 8,492,578 B2

COMPOUNDS USEFUL IN THERAPEUTIC AND COSMETIC METHODS

This application claims the benefits under 35 U.S.C. 119 (a)-(d) or (b), or 365(b) of International Application No. PCT/IB2008/055272 filed Dec. 12, 2008; European Application No. 07123268.0 filed Dec. 14, 2007; and Swiss Application No. 1040/08 filed Jul. 4, 2008.

TECHNICAL FIELD

The present invention relates to novel compounds, to compounds for use in cosmetic methods and cosmetic products. The compounds can also be used as medicaments and in pharmaceutical products, and in methods of treatment and/or prophylaxis using such compounds. In particular, the present invention relates to compounds useful in photodynamic therapy for cosmetic and therapeutic indications.

PRIOR ART AND THE PROBLEM UNDERLYING THE INVENTION

Photochemotherapy, or also called photodynamic therapy (PDT), is a technique that is primarily known for the treatment, amongst others, of various abnormalities or disorders of the skin or other epithelial tissues or mucosae, for example cancers or pre-cancerous lesions and certain non-malignant lesions for example skin complaints such as psoriasis. Furthermore, photodynamic therapy is also used for purely cosmetic purposes such as the removal of unwanted hair, reported in WO03/041673, or the treatment of greasy skin. Photochemotherapy involves the application of photosensitizing (photochemotherapeutic) agents to the affected area of the body, followed by exposure to light at a suitable wavelength in order to activate the photosensitizing agents and convert them into a cytotoxic form, whereby the affected cells are killed or their proliferative potential diminished or their metabolic status altered.

A photosensitizing agent may assert its effect by a variety of mechanisms, directly or indirectly. Thus, for example, certain photosensitizers become directly toxic when activated by light, whereas others generate toxic species, for example oxidizing agents such as singlet oxygen or oxygen derived free radicals, which are extremely destructive to cellular material and biomolecules such as lipids, proteins and nucleic acids.

Instead of applying a photosensitizing agent it is possible to use a photosensitizer precursor, a prodrug, which is transformed into a photosensitizer at the target site, for example by cells of the skin.

Protoporphyrin IX (PpIX) is a highly potent photosensitizer, which is synthesized from 5-aminolevulinic acid (ALA) as an intermediate product of the heme synthesis, for instance in skin cells. Then, the enzyme ferrochelatase introduces iron ($Fe^{3+}$) into the PpIX molecule, thus forming heme and removing the photocytotoxic PpIX.

When ALA is topically applied onto the skin of an individual, it penetrates through the stratum corneum of the skin and leads to an accumulation of PpIX or related, natural porphyrins, in the underlying living skin cells. Since, amongst others, the action of ferrochelatase is a rate-limiting step in heme synthesis, an excess of ALA leads to a transient and localized build-up of PpIX. In the treatment of skin tumors this effect is exploited in that ALA is topically applied to the skin tumor and, a few hours later, the tumor is exposed to light and a beneficial photochemotherapeutic effect may be obtained.

One disadvantage of ALA is that it does not sufficiently penetrate into the tumor tissue. In U.S. Pat. No. 6,035,267 this problem is addressed in that an ALA-alkyl ester for topical application is disclosed. One problem of this approach is that the ALA alkyl ester also penetrates through the stratum corneum of normal, healthy skin. Light exposure following administration on the skin thus also damages healthy skin tissue. Currently, the ALA methyl ester, commercialised as Metvix®, is the only approved derivative of ALA in dermatology. In other words, PDT treatment with ALA and its current derivatives is hindered by its non-negligible side effects due to the unwanted delivery of therapeutic doses to the non-targeted skin. Furthermore, ALA-alkyl esters, in particular, the methyl ester of ALA have demonstrated non negligible allergenic potential (M. J. Harries et al. Photodermatology, Photoimmunology and Photomedicine. 2007 Vol. 23 No 1. pp 35-36/J M Jungersted. Contact dermatitis. 2008. vol 53. No 3. pp 184-186/Metvix Package leaflet:information for the user). ALA itself has not demonstrated such an allergenic potential. The allergenic potential of ALA-alkyl esters can be attributed exclusively to the alkyl chains linked to the ALA part of the molecules. The ALA itself is a body-owned molecule, which does not exhibit an allergenic potential. Indeed, many efforts have been made to increase the penetration through the skin by derivatization of the molecule in the hope of increasing PpIX production in the target tissue. These efforts largely ignore that by increasing penetration of photosensitizers through intact skin, healthy skin is adversely affected in the irradiation step conducted in photodynamic therapy or due to its skin irritation potential even in the absence of light such as an allergic effect.

It is an objective of the present invention to improve target specificity of photosensitizers or photosensitizer precursors in PDT.

Further, it is an objective to provide photosensitizers or photosensitizer precursors enabling a spatial selectivity between non-targeted, generally healthy skin and the target structure, which entails the sparing of this non-targeted tissue and reduces dramatically the side effects whilst treating the target tissue.

Further, it is an objective to provide photosensitizers or photosensitizer precursors which are non-allergenic.

In particular, it is an objective of the present invention to provide a photosensitizer or precursor that does not pass the stratum corneum but that is capable to produce PpIX or other natural porphyrins in the target tissue.

In a more general sense, it is a goal of the present invention to use PDT in therapeutic and cosmetic applications while avoiding or reducing side effects, such as skin irritation, in healthy skin.

Accordingly, it is an objective of the present invention to reduce side effects of PDT in cosmetic and/or therapeutic applications, in particular in the cosmetic and/or therapeutic treatment of psoriasis, acne, hair removal, epilation, depilation, hair growth inhibition, hair re-growth inhibition, seborrheic dermatitis, rosacea, cancer, precancer, greasy skins, hairs, dandruff, skin infections, modulation of skin healing, hyperhidrosis, and/or bromhidrosis.

SUMMARY OF INVENTION

Remarkably, the inventors of the present invention found that certain photosensitizers or precursors that are substantially or to a large degree incapable of passing the stratum corneum reach successfully certain target tissues and are thus particularly useful in various therapeutic and cosmetic applications of PDT. This is surprising in view of the many efforts that have been made previously to increase the penetration of photosensitizers and/or precursors through the skin. The compounds of the present invention are advantageous over compounds disclosed in the prior art, because healthy, intact skin is to a large degree impervious to the compounds of the invention and escapes damage following the irradiation step in photodynamic therapy or other irritation due to the presence of the substance. The compounds used in the methods and products of the present invention are thus more specific to altered skin tissue or skin appendices, which actually need treatment.

Accordingly, the present invention provides, in a first aspect, a cosmetic method for reducing undesired skin modifications associated with one or more selected from psoriasis, sebaceous gland related conditions including acne, seborrhoic dermatitis and rosaceae, greasy skin, greasy hair, dandruff, hyperhidrosis and bromhidrosis, the method comprising:

topically administrating onto an affected skin area of an individual suffering from said undesired skin modifications a composition comprising an effective amount of a photosensitizer and/or photosensitizer precursor (hereinafter: precursor), wherein said photosensitizer and/or precursor, when topically applied onto healthy, intact skin of an individual, is substantially incapable of passing through the stratum corneum of the individual, and exposing the skin of the individual suffering from said undesired skin modifications to light of a selected wavelength and intensity effective to induce death of skin cells having accumulated said photosensitizer and/or precursor.

In a second aspect, the present invention provides cosmetic composition for topical administration comprising a photosensitizer and/or photosensitizer precursor (hereinafter: precursor), wherein said photosensitizer and/or precursor is characterised in that, when topically applied onto the skin of an individual it is to a large extent incapable of passing through the stratum corneum of the individual.

In a third aspect, the present invention provides compounds for use as a medicament or as a cosmetic product, said medicament and/or cosmetic product being intended for topical administration in photodynamic therapy, wherein said compound is a photosensitizer and/or photosensitizer precursor (hereinafter: precursor), wherein said photosensitizer and/or precursor is characterised in that, when topically applied onto the skin of an individual it is to a large extent incapable of passing through the stratum corneum of the individual.

In a fourth aspect, the present invention provides the use of compounds of the invention in cosmetic methods and/or products, in particular methods and/or products for hair removal and/or hair growth inhibition. The compounds are also useful for inhibiting re-growth of a hair, for example following hair removal In a fifth aspect, the present invention provides a method of preventing and/or treating a dermatological disease by photodynamic therapy, the method comprising the step of topically administering to an area of the skin of an individual a compound of the present invention.

In a sixth aspect, the present invention provides method of preparing a photosensitizer or photosensitizer precursor for use in photodynamic therapy, the method comprising the steps of chemically modifying a photosensitizer or precursor to obtain a modified photosensitizer or precursor, characterised in that said modified photosensitizer or precursor is to a large extent incapable of passing the stratum corneum of the individual.

In a seventh aspect, the present invention relates to pharmaceutical and/or cosmetic compositions comprising the compounds of the present invention.

In further aspects, the present invention relates to compounds as defined and disclosed herein as such, in particular to compounds comprising as structural element or consisting of the structures of formulae (I), (1) to (12) as disclosed in the present specification.

In one aspect, the present invention relates to esters, thioesters and amides of 5-ALA and a natural molecule, said natural molecule comprising an —OH, —SH, —COOH or —NH$_2$ group, and/or a substituent comprising such a group, susceptible of being covalently bound to 5-ALA.

In yet another aspect, the present invention provides, a compound as defined or disclosed herein, which is a non-allergenic compound. The protocol for determining if a compound is non-allergenic for the purpose of the present specification is detailed in Example 37.

In another aspect, the present invention relates to compounds as defined and disclosed herein for use in cosmetic products and/or as medicaments.

In yet another aspect, the present invention provides compounds of the present invention in the treatment of microorganisms and viruses on the skin. The invention also relates to the treatment of disease conditions caused by such microorganisms and/or viruses.

In an aspect, the present invention relates to the cosmetic treatment of undesired skin modifications associated with one or more selected from psoriasis, sebaceous gland related conditions including acne, seborrhoic dermatitis and rosaceae, greasy skin, greasy hair, dandruff, hyperhidrosis and bromhidrosis.

In another aspect, the invention provides the therapeutic treatment of one or more conditions selected from psoriasis, sebaceous gland related conditions including acne, seborrhoic dermatitis and rosaceae, greasy skin, greasy hair, dandruff, hyperhidrosis and bromhidrosis.

In a further aspect, the present invention relates to diagnostic tools and methods of diagnosis said tools and method taking use of the compounds of the invention.

In a still further aspects, the present invention relates to the compounds of the present invention for use as medicaments, to methods of treatments in which the compounds are administered, to the compounds for use in the prophylaxis and/or treatment of pre-cancer and/or cancer.

Accordingly, the compounds of the present invention can be used in therapeutic as well as in non-therapeutic methods as defined herein.

Aspects and preferred embodiments of the invention are provided in the appended claims.

In the drawings,

FIGS. 1-10 are fluorescence images of human forearm or leg skin areas of 2.5 cm in diameter, the pictures being taken three hours after administration of different photosensitizer precursors under variable experimental conditions.

FIGS. 1A-B are fluorescence photographs of human skin to which compounds of the invention were applied. A formulation containing phenylalanin-ALA-amide (compound 1) at 80 wt. % was topically applied to the skin and pictures were taken 3 hours following administration. In FIG. 1A, skin was not pre-treated and fluorescence was measured with 20 milliseconds (ms) exposure time. In FIG. 1B, hair was mechanically removed by wax-epilation before administration of the formulation and fluorescence was measured with 10 milliseconds (ms) exposure time. Bright dots at the positions of hair follicles indicate spots of high fluorescence, where compound 1 has entered into the skin tissue through the breach opened in the stratum corneum by the mechanical removal of the hair shaft.

FIGS. 2A-B are photographs of skin as with FIG. 1. Instead of compound 1, the formulation contained 80 wt. % of 1'-α-D-glucose-ALA-ester (compound 11). In A, skin is untreated and exposure time was 20 ms, in B hair was mechanically removed as in FIG. 1 and exposure time was 10 ms.

FIGS. 3A-C are photographs of skin as with FIG. 1. Instead of compound 1, the formulation contained ALA-cholesteryl ester (compound 6) at 70 wt. %. In A, skin was untreated and exposure time is 20 ms. In B hair was mechanically removed and exposure time was 10 ms. In C, the skin was dry-shaved and exposure time was 10 ms.

FIGS. 4A and B are photographs of skin as with FIG. 1. Instead of compound 1, the formulation contained glycerol-tri-ALA-ester (compound 10) at 80%. In A, skin was untreated and exposure time was 20 ms. In B hair was mechanically removed and exposure time is 10 ms.

FIGS. 5A-C are photographs of skin as with FIG. 1. Instead of compound 1, the formulation contained Tyrosine-ALA ester (compound 2) at 20 wt. %. In A, skin was untreated and exposure time was 20 ms. In B hair was mechanically removed and exposure time is 10 ms. In C, the skin was dry-shaved and exposure time was 4 ms.

FIGS. 6A-C are photographs of skin as with FIG. 1. Instead of compound 1, the formulation contained Phloroglucinol-tri-ALA-ester (compound 7) at 20 wt. %. In A, skin was untreated and exposure time was 20 ms. In B hair was mechanically removed and exposure time was 10 ms. In C, the skin was dry-shaved and exposure time was 4 ms.

FIGS. 7A and B are photographs of skin as with FIG. 1. Instead of compound 1, the formulation contained ALA-Trichloroethyl-ester (compound 9) at 20%. In A, skin was untreated and exposure time was 20 ms. In B hair was mechanically removed and exposure time was also 20 ms.

FIGS. 8A-C are photographs of skin as with FIG. 1. Instead of compound 1, the formulation contained ALA-ethyl-ester-ALA (compound 8) at 20 wt. %. In A, skin was untreated and exposure time was 20 ms. In B hair was mechanically removed and exposure time was 10 ms. In C, the skin was dry-shaved and exposure time was 4 ms.

FIGS. 9A-C are photographs of skin as with FIG. 1. Instead of compound 1, the formulation contained ALA-cholesteryl-hexyl-ester (compound 5) at 20 wt. %. In A, skin was untreated and exposure time was 20 ms. In B hair was mechanically removed and exposure time was 20 ms. In C, the skin was dry-shaved and exposure time was 10 ms.

FIGS. 10A and B are photographs of skin as with FIG. 1. Instead of compound 1, the formulation contained ALA-ascorbate-ester (compound 12) at 80%. In A, skin was untreated and exposure time was 10 ms. In B, the skin was dry shaved and exposure time was 10 ms.

Figure 21:
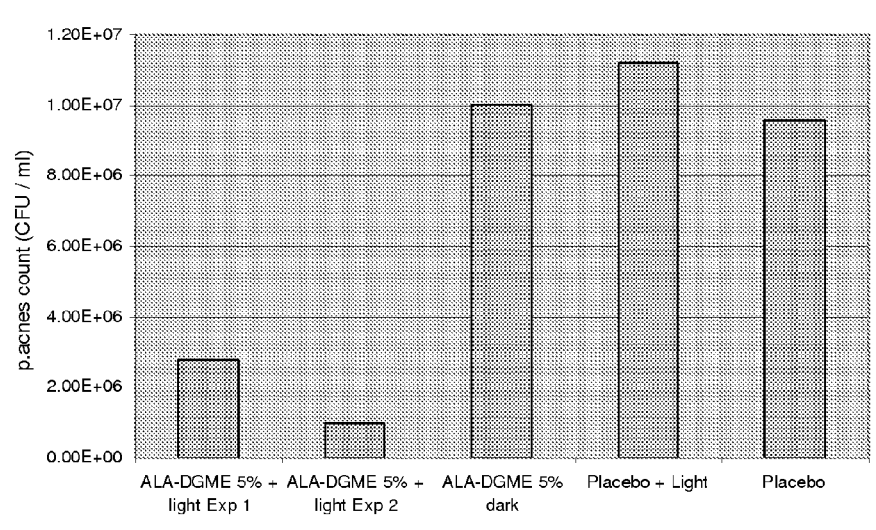

FIG. 21 shows the reduction in *Propionobacerium acnes* counts on a skin area of the face of an individual. Complete treatment involves topical administration of a formulation comprising ALA-DGME, followed by light exposure. The left two columns show that substantial reduction of bacterial counts is obtained by the treatment.

Figure 22:
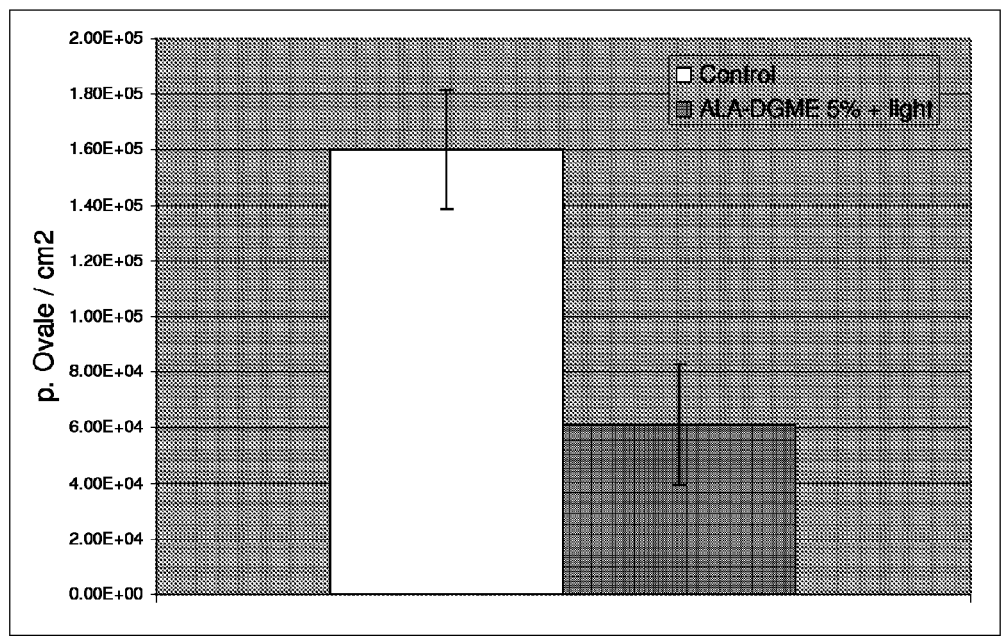

FIG. 22 shows the reduction in *Pytirosporum ovale* counts on a skin area on the face of an individual. Complete treatment involves topical administration of a formulation comprising 5 wt. % ALA-DGME, followed by light exposure. The left two columns show that substantial reduction of yeast counts is obtained by the treatment.

DETAILED DESCRIPTION OF THE PREFERRED EMBODIMENTS

The compounds of the present invention may be or comprise a "photosensitizer" and/or "photosensitizer precursor". For the purpose of the present specification the term "photosensitizer" refers to a compound, which increases photosensitivity of cells and/or tissues in which it accumulates. When cells and/or an entire tissue accumulating the photosensitizer are irradiated with light of a specific wavelength and/or intensity, cell death, changes in the cell's metabolitic activity and/or signalling are the preferred consequence. A "photosensitizer precursor", also referred to as a "precursor" herein, is a compound that is converted into or induces the creation of a photosensitizer when applied to cells and/or a tissue. For the purpose of the specification, the terms "photosensitizer" and "precursor" may be used interchangeably.

According to a preferred embodiment, a "photosensitizer" or "precursor" induces fluorescence of the cells and/or tissue that absorbs it.

According to an embodiment, the "photosensitizer" or "precursor" induces the accumulation of protoporphyrin IX (PpIX) or other photoactivable porphyrins in the cells/tissue to which it is administered. The accumulated PpIX or other natural porphyrin is fluorescent and its accumulation can thus be determined by measuring fluorescence.

Many "photosensitizers" have been described so far in the literature and can be selected by the skilled person. For example, photosensitizers include compounds comprising a structure selected from one or more of porphyrin, chlorin, bacteriochlorin, porphin, corrin, corphin, cyclodextrin phtalocyanin, benzoporphyrin and pyropheophoride, for example. Protoporphyrin and its derivatives, in particular propoporphyrin IX (PpIX) are known to function as photosensitizing agents. These compounds and suitable derivatives are thus encompassed by the present invention. Derivatives, for the purpose of the present specification, are compounds that comprise as a structural element the structures mentioned above, or which are obtained by chemically modifying these compounds while maintaining their photosensitizing properties.

5-aminolevulinic acid (ALA) is a well-known precursor of natural photosensitizing compounds such as PpIX and similar compounds. While not having photosensitizing properties as such, it is metabolised by cells that take it up to form photosensitizing compounds, in particular natural porphyrins. Accordingly, derivatives of ALA fulfilling the conditions of the present invention are preferred embodiments of "photosensitizers" of the present invention. Preferred embodiments of ALA-derivatives are provided further below.

For the purpose of the present specification, the use of the plural generally also refers to the singular and vice versa. For example, when reference to "compounds" is made, this may refer to a pure compound or a composition, such as a formulation for administration, comprising a purified compound. The present invention also encompasses compositions comprising two or more enantiomers, such a racemats and/or compositions of comprising two or more chemically different, unrelated active compounds. The term "active" refers to biological activity in the methods and uses of the present invention, including therapeutic and cosmetic methods.

The present invention provides compounds which, when topically applied onto the skin of an individual, are to a great degree incapable of passing through the intact, healthy stratum corneum of the individual, but active in the target tissue. This particularity of the compounds of the present invention could also be expressed by indicating that these compounds substantially accumulate in the intact, healthy stratum corneum or on its surface of the individual and/or in tissue of skin appendices such as the pilo-sebaceous apparatus of the individual, without penetrating through said stratum corneum. Another way of expressing this property of the compounds of the present invention is that stratum corneum of an average, healthy individual is to a great degree impervious to said photosensitizer or precursor.

For determining whether or not a compound fulfils this requirement, the procedure set out in Example 22 is employed. Preferably, the skin to be tested is the skin of the forearm of a healthy individual.

A quantity of 5-10 mg/cm² of "Cold cream" containing a concentration between 10 and 100% wt. of the active have to be applied on the skin during 3 hours with the help of the semi-occlusive dressing Tegaderm™ (1622W, 3M Healthcare, D-46325 Borken, Germany).

Accordingly, the photosensitizer's or precursor's characteristics of substantially or to a large extent not passing through the stratum corneum can be determined by assessing relative fluorescence of at least one fluorescent derivative or metabolite of said sensitizer or precursor, wherein said fluorescent derivative is present in the skin of said individual. More particularly, relative fluorescence ($f_{relative}$) is the fluorescence, following administration of the "photosensitizer", measured on skin with an intact, healthy stratum corneum divided by the fluorescence measured on skin from which the stratum corneum has been removed or a breach in the stratum corneum has been opened e.g. by mechanical removal of the hair shaft. This may be illustrated by formula (I) below:

$$f_{relative} = \frac{f_{intact} \times 100}{f_{st.\,c.\,removed}} \quad (I)$$

According to an embodiment of the present invention, for determining the photosensitizer's or precursor's characteristic of not passing through the stratum corneum, an amount of photosensitizer and/or precursor applied per skin area, and a time interval following administration before assessing fluorescence are predetermined, and an amount of increased fluorescence caused by the administration of said photosensitizer or precursor is determined.

The removal of the stratum corneum is achieved by scraping the stratum corneum off, for example using a razor blade, as described in Example 22.

Fluorescence is measured 3 hours following topical administration.

Compounds are considered not being capable of penetrating through the stratum corneum of an individual, if the relative fluorescence intensity induced by a compound on a skin area is ≦40% of the fluorescence intensity obtained when the same amount of said compound is applied on a skin area from which the stratum corneum has been removed. More preferably, the compounds are not capable of passing the stratum corneum if said relative fluorescence intensity is ≦30%, more preferably ≦20%, and most preferably =10% of the fluorescence intensity of the compound applied on skin from which the stratum corneum is removed.

In case that the photosensitizer and/or photosensitizer precursor is not fluorescent and/or does not give rise to the accumulation of a fluorescent photosensitizer, another method for determining if a compound is incapable of passing through the stratum corneum of the individual can be used. The penetration of the photosensitizer through the stratum corneum can be determined by detecting the quantity of singlet oxygen produced during a photodynamic therapy treatment after topical administration of the photosensitizer on intact skin or skin with stratum corneum removed. The detection of singlet oxygen can be performed using for example infrared luminescence methods (Baier Journal of investigative dermatology. 2007. vol. 127. pp. 1498-1506). For determining if a photosensitizer or a precursor is incapable of passing through the stratum corneum the same percentages as indicated above for fluorescence are applied to luminescence according to this method.

According to an embodiment, the compound of the present invention comprises ALA, covalently bound to a natural molecule. A natural molecule, for the purpose of the present invention is any substance physiologically produced by any biological, living entity or physiologically participating to any biological entity's metabolism.

Preferably, a natural molecule, for the purpose of the present specification includes any substance produced by human cell metabolism, including substances that the human body is able to assimilate and/or to convert into an endogenous compound.

Furthermore, a natural molecule includes any substance produced by humans, animal and/or plants. This includes any substance able to be assimilated by plants or animals and be entirely converted into an endogenous compound of the said plant or animal.

The term "natural molecule" thus includes all compounds related to a biological process in humans, animals or plants, in particular to any substance found in any animal or plant cell in standard physiological conditions.

More preferably, a natural molecule concerns more specifically compounds that form part of human nutrition, in particle macronutrients and micronutrients, such as vitamins.

According to a preferred embodiment, the natural molecule is not immunogenic.

Examples of natural molecules are alcohols, for example glycerol, carbohydrates including mono, di, tri, oligo and polysaccharides, in particular sugars, such as glucose, fructose, galactose, riboses, mannose, and so forth, non-proteinogenic and proteinogenic amino acids, such as cystein, tyrosin, phenylalanin, methionin, and so forth, peptides such as di-peptides, tri-peptides, oligopeptides and/or polypeptides, vitamins such as vitamin E, vitamin A, vitamin C, vitamin D and so forth, nucleosides and nucleotides such as adenosine-tri-phosphate (ATP), AMP, ADP, cAMP, deoxyadenosine-tri-phosphate, GTP, GDP, GMP, CTP, CDP, CMP and so forth, DNA and RNA, lipids, including fatty acids, such as long-chain fatty acids ($\geqq$C18), such as linoleic acid, palmitic acid, medium chain fatty acids (C8-C16) and short chain fatty acid (<C8), and other lipids such as ceramides, sphingosides, squalen, and cholesterol, for example.

ALA derivatives of the present invention encompass esters of ALA (body-owned, non-allergenic) and a natural molecule, which is expected to have a low allergenic potential compared with alkyl chains of standard approved ALA-alkyl esters. In particular, it is expected that an ester of ALA and another natural body-owned molecule would have a very low allergenic potential.

Natural molecules, for the purpose of the present invention, also include hormones, such as steroids and peptide hormones. Natural molecules also include terpenes, including sesqui-, mono-, di- and triterpenes, and alkaloids, for example.

The natural molecule needs to comprise a functional group that can be covalently linked to 5-ALA, for example to the carboxylic group (—COOH) and/or the amino group (—NH$_2$) of 5-ALA. This functional group may be part of the natural molecule itself or of a optional substituent of the natural molecule, wherein said substituent does not need to be a natural molecule as defined herein. Preferably, the natural molecule (and/or its optional substituent) comprises at least one selected from: an hydroxyl group —OH susceptible of producing an ester by reaction with the carboxylic group of 5-ALA; an amine function susceptible of producing an amide by reaction with the carboxylic group of 5-ALA; a carboxylic function R—COOH susceptible of producing an amide by reaction with the amine functional group of 5-ALA; a thiol functional group R—SH susceptible of producing a thioester by reaction with the carboxylic group of 5-ALA. Compounds comprising an —OH group include primary, secondary and tertiary alcohols, enols and phenols for example. Compounds comprising a thiol are compounds comprising a thiolic, enethiolic and/or phenethiolic function for example. Compounds comprising an amine are primary, secondary, tertiary amines and/or enamines for example.

According to an embodiment, the compound of the present invention is selected from an ester, a thioester and/or an amid of 5-aminolevulinic acid (ALA, or 5-ALA).

According to a preferred embodiment of the present invention, the ALA-ester used in the context of the present invention is a glycol and/or a polyglycol ester. Such compounds are disclosed in WO 03/041673, which is expressly incorporated herein by reference.

According to a preferred embodiment, the compound of the present invention is a compound of formula (I):

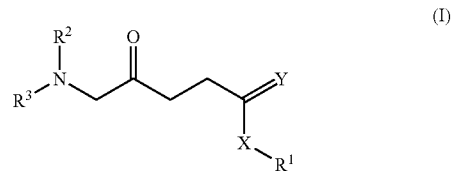

wherein:
Y is selected from S and O;
X is selected from O, NH, and S;
and R$^1$-R$^3$ are independently selected from H and from hydrocarbons comprising from 3-200 carbons and may contain one or more heteroatoms, wherein said heteroatoms may be selected from O, N, S, P, halogen (F, Cl, Br, I) but also from metal atoms, with the proviso that at least one of R$^1$-R$^3$ is not hydrogen. Metal atoms may be selected from Fe Mg, Si, Ge, and Ru, for example, and may be charged and/or bound by one or more complexing bonds to said hydrocarbon. Preferably, such metals have the oxidation number +2.

An example of a substituent R$^1$-R$^3$ selected from a hydrocarbon comprising a metal atom is chlorophyll, wherein the metal atom is Mg$^{2+}$. Chlorophyll may be selected from any chlorophyll type, for example, from chlorophyll a, b, c1, c2, d, or chlorophyllin, a semi-synthetic variant of chlorophyll. In particular, one of the carboxyl groups of the chlorophyll can be connected to the amine group of ALA, thereby obtaining the corresponding amide.

Alternatively, one of the cyclic amino groups of chlorophyll can be linked to the carboxyl group of ALA, also yielding an amide.

For example, one, two or all three of R$^1$-R$^3$ are different from hydrogen.

According to an embodiment, two of R$^1$-R$^3$ are hydrogen and one is a hydrocarbon as defined above. According to an embodiment, R$^3$ and R$^2$ are H and R$^1$ is a hydrocarbon as defined above.

Preferably, at least one selected from R$^1$-R$^3$ comprises from 0-40 heteroatoms.

Preferably, the at least one substituent selected from R$^1$-R$^3$ which is not H is selected from hydrocarbons comprising from 3-100 carbons and zero (0), one or more heteroatoms, preferably, 1-20 heteroatoms.

More preferably, the at least one substituent selected from R$^1$-R$^3$ which is not H is selected from hydrocarbons comprising from 3-35 carbons and zero (0), one or more heteroatoms, preferably, from 1-10 heteroatoms.

Most preferably, the at least one substituent selected from R$^1$-R$^3$ which is not H is selected from hydrocarbons comprising from 4-30, for example 5-20 carbons and zero (0), one or more heteroatoms, preferably 1-5 heteroatoms.

According to an embodiment, the at least one substituent selected from R$^1$-R$^3$, which is not H comprises, as a structural element, at least one natural molecule as defined herein, or, if the natural molecule is substituted, at least one substituted natural molecule as defined herein. For example, —X—R$_1$ comprises at least two, for example 3 natural molecules as structural elements.

According to an embodiment, X is part of the natural molecule or, if the natural molecule is substituted, may be part of the substituent of the natural molecule.

According to an embodiment, the substituent —X—R$_1$, —R$^2$ and/or R$^3$ is the natural molecule as defined herein above or the natural molecule as further substituted. Accordingly, X may be a heteroatom of the natural molecule, or, if applicable, of the substituent of the natural molecule.

If the natural molecule is substituted, the substituent is preferably a C0-C30 hydrocarbon comprising 1-5 heteroatoms, more preferably a C1-C10 hydrocarbon comprising 1-3 heteroatoms. Substituents may be selected, independently, from functional groups, such as —OH, —NH$_2$, =O, —SH, —COOH, —S(=O)$_2$OH (sulfonate, sulfonic acid), —O—P=O(OH)$_2$ (phosphate, phosphonic acid), halogen (F, Cl, Br, I), and from C1-C20 alkyl, C4-C20 aryl, C2-C20 alkenyl, wherein said alkyl, aryl and alkenyl may comprise one or more heteroatoms and/or may be further substituted, for example with one or more selected from the functional groups indicated above, with the proviso that aryl, if it is C4, comprises at least one hetero ring-atom, so as to provide a substituent with aromatic properties. The aryl may thus be pyrimidine (C4), thiophene (C4), for example. C5 awls include pyridine, and, without any heteroatom, the cyclopentadienyl anion. If the substituent is an alkyl or an alkenyl, it may be linear, branched or cyclic, with the proviso that it has at least 3 carbons if it is branched or cyclic. Substituents may also be further substituted with further natural molecules (including substituted natural molecules) as defined herein.

If —X—R$^1$ is a natural molecule as defined herein, which is further substituted, X may represent a heteroatom of the natural molecule or of said substituent. In other words, the natural molecule may be connected by way of one of its possible substituents to the basic ALA structure of formula (I). For example, in the case of ALA-Cholesterylhexyl ester (compound 5 below), the natural molecule (cholesterol) is substituted with 6-hydroxyhexyl, and the substituent is connected, under formation of an ester bond, with the 6-hydroxy group, to the basic ALA structure of formula (I).

The substituent of the natural molecule thus may function as a linker for attaching the natural molecule to the ALA structure. A linker may thus be present, having the same definition as the substituent of the natural molecule given above.

In the case of compound 7 below, —X—R$^1$ is phloroglucinol, further substituted at its two remaining hydroxy groups with two further ALA, respectively. In this case, phloroglucinol is regarded as the substituent of one of the two further ALAs (natural molecule), wherein the substituent (phloroglucinol) is further substituted with a natural molecule (with a further ALA substituent). In compound 7, —X— is O and R$_1$ is a C16 hydrocarbon comprising 6 O and 2 N heteroatoms.

Preferably, the present invention excludes the possibility that R$^1$ is alkyl, in particular methyl, and in particular so when R$^2$ and R$^3$ are H. Such compounds are disadvantageous due to their allergenic potential, Examples of compounds of the present invention are provided below:

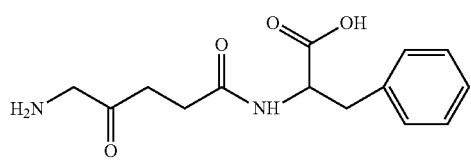
(1)

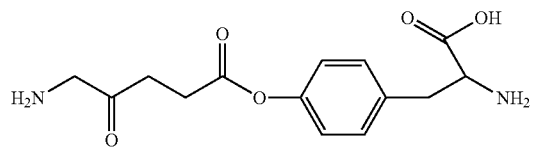
(2)

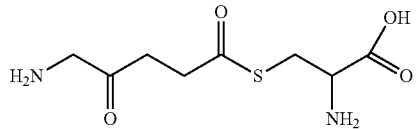
(3)

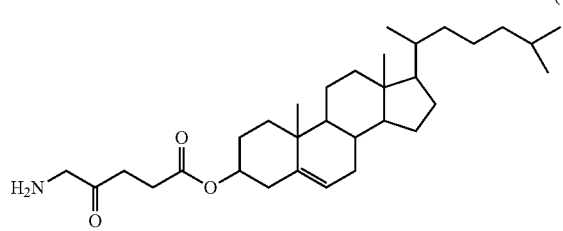
(6)

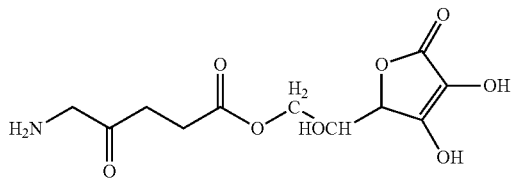
(12)

The present invention also relates to compounds (1)-(12) above, as well as compounds comprising, as a structural element, the structures of compounds (1)-(12) above.

For the purpose of the present specification the term "comprising" is intended it to mean "includes amongst other". It is not intended to be construed in as "consists only of".

As indicated above, the compounds of the present invention, according to preferred embodiments, are preferably esters of ALA. These compounds may be formed by esterification with a suitable alcohol of choice, contributing to the required properties to the overall compound. The conditions for esterification reactions will depend of the alcohol used and may be chosen such that maximum yield of the ester is obtained. Since the esterification reactions are reversible equilibrium reactions, reaction conditions may be selected in such a way that maximum yield of the ester product is obtained. Such conditions may be obtained by selecting a solvent which is capable of removing the water formed in a typical esterification reaction by forming azeotrops with water, e.g. some chlorinated hydrocarbons such as chloroform. For the formation of the lower esters of 5-ALA the equilibrium reaction may be driven to the ester side by using a large excess of the alcohol. With other esters the equilibrium may be driven towards the ester product by using a large excess of acid.

Esterification reactions are well known in the art for example, as described by Saul Patai "The Chemistry of the carboxylic acids and esters" (Ch. 11, p. 505, Interscience 1969) and Houban Weyl (Methoden der Organischen Chemie, Band E5, "Carbonsäuren and Carbonsäurederivate", p. 504, Georg Thieme Verlag 1985). The formation of derivatives of amino acids are described in Band XI/2 of the same series (Houben Weyl, Methoden der Organischen Chemie, Band XI/2, "Stickstoffverbindungen", p. 269, Georg Thieme Verlag, 1985).

With certain starting materials, the addition of protective groups may be necessary before starting the esterification reaction as such. Such a procedure is disclosed, for example, by Stephen Caddick, Alexandra K. de K. Haynes, Duncan B. Judd and Meredith R. V. Williams. Convenient synthesis of protected primary amines from nitriles. Tetrahedron Letters Volume 41, Issue 18, 29 Apr. 2000, Pages 3513-3516. Accordingly, these procedures may be used to temporarily protect groups potentially interfering with the desired esterification.

The compounds of the present invention are preferably used for topical application. Preferably, the compounds are epicutaneously applied on the skin of a human or animal. The compounds of the present invention may be formulated within any suitable exipient, for example standard excipients of the European Pharmacopoeia, for example "Cold cream" as described in example 12. Compounds may also be suspended in pure glycerol (GLY) or in pure diethylene glycol monoethyl ether (DGME), or other suitable, pharmaceutically acceptable suspension media, for example. In the examples, a few suitable formulations are provided without limiting in any way the scope of the invention.

The formulation, which may be a formulation of a cosmetic product or of a therapeutic product, may comprise 1-90 wt. %, preferably 3-85 wt. %, more preferably 5-80 wt % and even more preferably 8-70 wt. % of the compounds of the present invention. For the purpose of the present specifications, percentages in formulations and products are percentages by weight, unless otherwise indicted.

In the cosmetic, prophylactic and therapeutic methods of the present invention, preferably, 2-15, more preferably 4-11, even more preferably 5-10 and most preferably 7-8 mg of the formulation may be applied per $cm^2$ of skin.

The compounds of the present invention have the property of being to a large degree incapable of passing through intact stratum corneum of an individual as defined above. In particular, the compounds of the present invention generally pass through skin tissue characterized by a damaged or otherwise non-functional stratum corneum, as it appears with various conditions. The compounds of the present invention are also capable of accumulating in the skin appendices such as the pilosebaceous apparatus.

The property of the compounds of the invention to be repelled by intact stratum corneum renders them particularly suitable for cosmetic and therapeutic applications characterized by damaged stratum corneum, in which the protective function of the stratum corneum is at least to some extent diminished compared to the healthy state.

At the same time, the compounds of the present invention, being repelled by intact skin to a large degree, but readily absorbed in skin having a damaged stratum corneum, are advantageous over compounds disclosed in the prior art, due to their specificity and/or selectivity for damaged skin. Actually, the prior art consistently suggests that permeability of photosensitizers used in photodynamic therapy through the skin should be increased. This is contrary to the present invention, which achieves less damage to healthy tissue in photodynamic therapy by preventing the photosensitizers from reaching healthy tissue and from rendering it thus sensitive to photochemical damage.

Accordingly, the compounds of the present invention may be used in cosmetic products and/or as medicaments, in particular for treating or preventing unaesthetic and/or undesired conditions of the skin, but also for the treatment of diseases of the skin. According to an embodiment, the compound is used in the prevention and/or treatment of (1) skin cancer and/or skin precancer, (2) sebaceous gland related indications, and/or (3) psoriasis, wherein sebaceous gland related indications comprise acne, seborrhoic dermatitis, and rosaceae.

According to an embodiment of the cosmetic method and the cosmetic product of the invention, the method and/or product are non-therapeutic.

The effectiveness of the compounds of the present invention in the treatment of cancer and/or precancer derives from the phototoxic properties of the photosensitizers of the present invention. Accordingly, the characteristics of the compounds of the invention to induce photosensitizer fluorescence in tissue in which they accumulate reliably indicates the compounds' phototoxicity and hence its effectiveness in photodynamic therapy. The fluorescence induced by the compounds of the present invention stems, for example, from PpIX or other, structurally related natural porphyrin compounds.

The compounds of the present invention are useful in the cosmetic and also therapeutic treatment or prevention of greasy skins/hairs, dandruff and hyperhidrosis/bromhidrosis.

According to another embodiment, the compound of the present invention is used in the treatment of microorganisms and viruses on the skin.

The compounds of the present invention are particularly useful in cosmetic methods, including methods for hair removal and/or hair re-growth inhibition and/or hair growth inhibition. Preferably, while the compounds disclosed and defined herein do not pass through intact stratum corneum, they preferably accumulate in the pilosebaceous apparatus and/or the hair follicle in the skin of a human or animal subject. Accordingly, the compounds of the present invention preferably have a high selectivity for the pilosebaceous apparatus and/or the hair follicle, in particular after the mechanical removal of the hair shaft.

The compounds of the present invention are also useful in diagnostic methods. In particular, the compounds are advantageous where the improved selectivity is important. For example, the compounds may be used for one or more selected from tumor demarcation, tumor detection, and identification of microbe infections.

The present invention is illustrated by way of the following examples, which serve for illustration of the general concept of the present invention without limiting its scope.

EXAMPLES

In the present examples, percentages are by weight unless otherwise indicated.

Examples 1-12

Synthesis of Compounds According to the Invention

All raw materials for conducting the synthesis Examples 1-11 were obtained from Sigma-Aldrich Chemie, 9471 Buchs, Switzerland.

1. Phenylalanine-ALA-amide

Aminolevulinc acid is dissolved in methanol with dibromide. Then, the product is purified and dissolved in methanol under hydrogene flow. Palladium is used as a catalyser, then Boc2O is added. The addition of hexafluorobenzene allows obtaining a pentafluorobenzene ester which is easily substituted by Phenylalanine The Boc protected Phenylanine-ALA-ester derivative is deprotected in acidic conditions and the final product (compound 1) is purified by chromatography.

2. Tyrosine-ALA-ester

Tyrosin is dissolved in ethanol and esterified with a ter-butyl group then re-crystallized and dissolved in dichloromethane. Boc2O is added to achieve protection of the amine group. ALA protected by a Boc function on its amine group is left for reacting with DCC and DMAP with the protected Tyrosine which has been previously re-crystallized. The protected Tyrosin-ALA-ester is de-protected in TFA to obtain the Tyrosin-ALA-ester (compound 2) derivative which can be purified by chromatography.

3. Cystein-ALA-ester

Cystein is esterified by a ter-butyl group and placed in oxidant conditions in order to produce a cystein dimere linked by a disulfide bond. The dimere is then dissolved in dichloromethane and Boc protected on its amine groups. The protected dimere is placed on reducing conditions to release two protected cysteins and left for reacting with ALA which has been previously Boc protected on its amine function. The protected ALA-cystein derivative is obtained after thioesterification and deprotection is achieved in TFA. The ALA-cystein-thioester derivative (compound 3) is purified by chromatography.

4. ALA-Oxazepam-hexyl-ester

In a first step, ALA which has been previously Boc protected on its amine function, is esterified with 1-bromo-hexanol with DCC and DMAP. An addition is then realized between the Boc-ALA-bromohexyl ester and the hydroxyle group of the Oxazepam molecule. The resulting Boc protected ALA-Oxazepam-hexyl-ester is then de-protected in TFA and can be purified by chromatography (compound 4).

5. ALA-Cholesterylhexyl-ester

In a first step, an ester of Cholesterol and Hexanol is obtained by the reaction of Cholesterol with 1-Bromo-hexanol in the presence of sodium hydrure. The product is then esterified, with DCC and DMAP, with ALA which has been previously Boc protected on its amine group. The Boc protected ALA-Cholesterylhexyl-ester is then de-protected in TFA and ALA-Cholesterylhexyl-ester (compound 5) can be purified by chromatography.

6. ALA-Cholesteryl-ester

Cholesterol is esterified with ALA which has been previously Boc protected on its amine group with DCC and DMAP. The Boc-ALA-Cholesteryl-ester is de-protected in TFA and the final ALA-Cholesteryl-ester (compound 6) can be purified by chromatography.

7. Phloroglucinol-tri-ALA-ester

Phloroglucinol is esterified with ALA which has been previously Boc protected on its amine group with DCC and DMAP. The $Boc_{(3)}$-Phloroglucinol-tri-ALA-ester is de-protected in TFA and the final Phloroglucinol-tri-ALA-ester (compound 7) can be purified by chromatography.

8. ALA-ethyl-ester-ALA

ALA which has been previously Boc protected on its amine group is left with DCC and DMAP for reacting with ethylene glycol to obtain a di-ester of ALA (with the two hydroxile groups of the ethylene glycol). The protected $Boc_{(2)}$ALA-ethyl-ester-ALA is de-protected in TFA and the final ALA-ethyl-ester-ALA (compound 8) can be purified by chromatography.

9. ALA-Trichloroethyl-ester

ALA which has been previously Boc protected on its amine group is esterified with 1,1,1-tri-chloroethanol with DCC and DMAP. The protected Boc-ALA-Trichloroethyl-ester is de-protected in TFA and the final ALA-Trichloroethyl-ester (compound 9) can be purified by chromatography.

10. Glycerol-Tri-ALA-ester

Glycerol is esterified with ALA which has been previously Boc protected on its amine group with DCC and DMAP. The $Boc_{(3)}$-Glycerol-tri-ALA is then de-protected in TFA to release the final Glycerol-tri-ALA (compound 10) which can be purified by chromatography.

11. 1-Glucose-ALA-ester

In a first step, Glucose is entirely protected on its hydroxyl groups using benzyl bromide. The benzyl group in position 1' is then selectively deprotected using enzymatic catalysis. ALA which has been previously Boc protected on its amine group is added and left for esterification with the free hydroxyl group of the benzyl-protected glucose. Benzyl and Boc residues are then removed using TFA. The final 1'-α-D-Glucose-ALA-ester (compound 11) can be purified by chromatography.

12. ALA-ascorbate-ester

Ascorbic acid is esterified with ALA which has been previously Boc protected on its amine amine group with DCC and DMAP. The Boc-ALA-ascorbate-ester is de-protected in TFA and the final ALA-ascorbate-ester (compound 12) can be purified by chromatography.

Examples 13-21

Formulations for Topical Application

Various formulations for topical administration of compounds 1-12 were produced based on the indications given below, in which percentages are percent by weight. Once prepared according to the quantities indicated below, all formulations were supplemented with a respective compound of the present invention. In general, 20 parts by weight of purified ingredient were added per 100 parts by weight of final formulation.

13. Cold Cream (Oil in Water Emulsion)

Cetylic alcohol 21%, liquid paraffin 19%, Span® 80 0.5%, Tween® 80 4.5%, water 55%.

14. Ointment with Lanoline

Adeps lanae (Lanoline) 37.5%, Vaselinum album (vaseline) 62.5%

15. Hydrogel

Carboxymethylcellulosum Na 450cps (Carbopol) 3.5%, water 96.5%.

16. Anionic Hydrophilic Cream (Oil in Water Emulsion)

Cetylanum 5%, Arachidis oleum raffinatum (purified peanut oil) 30%, Propylene glycol 20%, water 45%.

17. Non Ionic Hydrophilic Cream (Oil in Water Emulsion)

Tween® 80 5%, Propylene glycol 10%, cetylic alcohol 10%, Arachidis oleum raffinatum (purified peanut oil) 30%, water 45%.

18. Lipophilic Ointment

Liquid parraffine (5%), Vaselinum album (vaseline) 95%.

19. Unguentum Leniens (Water in Oil Emulsion)

Cera alba (white wax) 8%, Arachidis oleum raffinatum (purified peanut oil) 72%, sodium dodecyl sulphate 0.1%, water 19.9%.

20. Mild II Cream (Water in Oil Emulsion)

Cetylic alcohol 0.85%, Adeps lanae (Lanoline) 3%, Vaselinum album (vaseline) 12.9%, Cera alba (white wax) 1.5%, Arachidis oleum raffinatum (purified peanut oil) 34%, water 47.75%.

21. Nanoemulsion

Arachidis oleum raffinatum (purified peanut oil) 65%, Tween® 80 7%, Span® 80 22%, propylene glycol 3%, water 3%.

Example 22

Methodology and Equipment for Measurement of the Permeability of Compounds of the Invention Through the Stratum Corneum Permeability of compounds of the invention through the stratum corneum is assessed by measurements of fluorescence of PpIX. The expression "PpIX", for the purpose of the present specification, stands for PpIX as reported in the literature and other natural porphyrins producing a fluorescent signal following illumination with suitable light. Permeability of the compounds of the present invention is determined by comparing PpIX-induced fluorescence of compounds of the invention applied on the surface of intact skin with fluorescence induced by the same compounds applied on skin from which the stratum corneum has been removed.

The stratum corneum was removed by dry shaving with a razor blade (BIC Classic 1 lame). The lame is gently swept 8 times over the skin without using water, razor foam or any other lubricant.

Formulations comprising compounds of the invention and controls are administered topically on the forearm or the leg using the Tegaderm™ transparent dressing. This dressing enables the transport of water and oxygen according to the specifications of the manufacturer. This dressing was removed and the remaining formulation cleaned with water just before the measurements.

A fluorescence imaging system illustrated in FIG. IX of WO 03/041673 is used to assess the extent and level of PpIX production in "macroscopic" samples (parts of the human body such as: forearm, leg, back, etc.). The experimental equipment and descriptions, as well as the ALA-DGME compounds disclosed therein are expressly incorporated herein by reference. As the goal is to assess the relative level of PpIX, red light at 635 nm is chosen as PpIX fluorescence excitation wavelength. It is indeed well known that red light penetrates deeper in the cutaneous tissues than green and violet light, the later two wavelengths corresponding to larger PpIX absorption peaks (see the PpIX fluorescence excitation and emission spectra presented on the right side in FIG. IX of WO 03/041673).

As presented in the schematic diagram presented in FIG. IX of WO 03/041673, this fluorescence imaging system involves a modified 300 W D-light source 1 (Xe arc lamp from Storz, Tuttlingen, Germany) equipped with a red bandpass filter (635 nm, 20 nm FWHM; Chroma, USA). This fluorescence excitation light is coupled in a Storz 4 mm diameter light guide 2. The output of this light guide is imaged on the tissue sample 3 with a projection objective 4 (Nikon, Japan; A F Nikkor; 1:1.4 D/50 mm) to generate a homogenous spot of 2.5 cm in diameter with an irradiance of 2 mW/cm$^2$ at 635 nm. The distance between this projection objective 4 and the sample 3 is 25 cm. Therefore, the light beam illuminating the sample can be considered as parallel. The fluorescence is collected by another objective 5 (Fujinon, Japan; TV zoom lens; 1:1.2/12.5-75 mm; Type H6X12.5R-MD3) through a longpass filter 6 (Schott, Germany; RG665) and the image detected by a scientific CCD camera (752×582 pixels CF 8/1 Kappa, Gleichen, Germany) equipped 7 with an image intensifier (Proxifier BV 256-2FcZ-CH, Proxitronic, Bensheim, Germany). The images are captured by the 8-bits camera frame grabber and saved on the computer 8 with the "Kappa Imagebase-control" software. Image treatment is carried out using the IPLab imaging software. The spatial resolution of the complete setup has been measured with an USAF resolution target and the value we obtained in the sample plan is 3 lp/mm, the size of the image detected by the camera being 3×4 cm$^2$.

A reference sample is been designed to enable a comparison of the relative fluorescence brightness between samples investigated at different times. This reference consists of a ruby disk (diameter: 12 mm; thickness: 1.02 mm; Type 8Sp3, Hans Stettler S A, Lyss, Switzerland) covered with a neutral density filter (T=2.27%) so that the signal obtained with this reference sample corresponds to the typical tissue fluorescence detected in our conditions. The images are analyzed using the NIH image software. The method consisted in identifying the location of an area corresponding to: 1) epidermis presenting no hair follicles and 2) the hair follicles. Measurements (1) will be relevant for assessing permeability through the stratum corneum. The number of pixels involved in such an area are 100. The value of these pixels are averaged, corrected by subtracting the tissue autofluorescence recorded at a location which did not received any PpIX precursor. Thus, for each tested formulation, areas surrounding a hair follicle receive a fluorescence brightness value and areas of the epidermis bearing no hair (epidermis) also receive a fluorescence brightness value, these values being expressed in arbitrary relative units, relative to the reference being the above-mentioned ruby disk. The ratio r=fluorescence brightness value of a hair follicle area/fluorescence brightness value of a hairless epidermis area is used to quantify the selectivity of the compounds of the invention towards the hair follicle.

Examples 23-32

Measurements of Fluorescence Induced by Compounds of the Present Invention

Compounds 2, 5, 6, 7, 8, 11 and 12 described above were mixed in a "Cold cream" as formulation as described in Example 13 above.

Table 1 shows fluorescence values obtained of compounds of the invention on skin which was left intact and from which the stratum corneum (SC) has been removed by dry shaving.

TABLE 1

| Compound | Skin treatment | Fluoresence epidermis | Penetration through epidermis (%) | Example |
|---|---|---|---|---|
| 6 | No | 1 | | 23 |
| | SC removed | 25 | 4% | 23 |
| 2 | No | 0 | | 24 |
| | SC removed | 114 | 0% | 24 |
| 11 | No | 0 | | 25 |
| | SC removed | 12 | 0% | 25 |
| 7 | No | 30 | | 26 |
| | SC removed | 187 | 16% | 26 |
| 8 | No | 30 | | 27 |
| | SC removed | 225 | 13.3% | 27 |
| 5 | No | 7 | | 28 |
| | SC removed | 94 | 7.44% | 28 |
| 12 | No | 4 | | 29 |
| | SC removed | 20 | 20% | 29 |
| ALA | No | 31 | | 30 |
| | SC removed | 52 | 59.6% | 30 |
| ALA-DGME | No | 20 | | 31 |
| | SC removed | 57 | 35.1% | 31 |
| Hexyl-ALA-ester | No | 37 | | 32 |
| | SC removed | 88 | 42% | 32 |

In Table 1, ALA-DGME stands for diethylene-glycol monoethyl ether ester of ALA.

Values obtained with compounds applied onto intact skin (no skin treatment) can be compared with values from which stratum corneum has been removed to assess permeability.

It can be seen with compound 6, for example, that removal of the stratum corneum increases fluorescence 25 fold, which indicates that this compound does not penetrate through the stratum corneum.

With compound 8, fluorescence upon removing the stratum corneum has increased by a factor of 7.5, the fluorescence induced by compound 8 thus representing only 13.3% of fluorescence obtained by the compound applied on skin from which the stratum corneum has been removed. Again, this compound is largely incapable of diffusing through the stratum corneum and thus falls in the definition of the present invention.

Example 33

Photodestruction of the Bacterium *Propionobacterium acnes* (*P. acnes*) Immediately after PDT using ALA-DGME 5%

Strong reduction of bacteria and yeast population on the face of humans without affecting the skin is possible with selective ALA-derivatives used for in vivo PDT as is illustrated.

ALA-DGME 5% is prepared in Cold cream. 15 mg of 5% ALA-DGME in Cold cream or placebo (Cold cream) are applied to the face of a volunteer. 3 hours later, the zone, which received ALA-DGME or placebo is exposed to 5-15 J/cm$^2$ of red light. Immediately after illumination, the bacteria present on the administration zone are collected by immersion in a collection buffer allowing bacteria to detach and survive in suspension. Collection samples are inoculated, after suitable dilution, on agar plates, which are selective for *p. acnes*. CFU (Colony Forming Units) are counted after 5 days of growth on selective medium.

Figure 20:
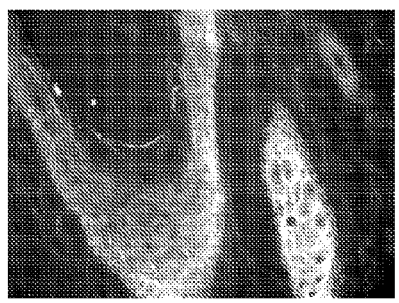
FIG. 20 is a microscopic image of fluorescence in sebaceous gland in a tissue sample after application of a formulation comprising 20 wt. % ALA-DGME. This figure shows the selectiveness of the compounds of the present invention.

The results are shown in FIG. 20. It can be seen that ALA-DGME, a compounds of the present invention, when topically applied, is suitable to kill microorganism present on the skin of an individual. No adverse reaction was observed on the skin of the volunteer.

Example 34

Photodestruction of the Yeast *Pytirosporum ovale* (*P. ovale*) 24 Hours after PDT using ALA-DGME 5%

ALA-DGME 5% is prepared in Cold cream as in the previous example. 15 mg of 5% ALA-DGME in Cold cream or placebo (Cold cream) are applied to the nose of a volunteer suffering from seborrheic dermatitis. 3 hours later, the zone, which received ALA-DGME or placebo is exposed to 5-15 J/cm$^2$ of red light. 24 hours after the end of the light exposure, scales are collected using a patch-strip method (D-Squame. Cuderm Corp. Dallas. US) and *P. ovale* can be counted under fluorescence microscope using a fluorochrome which is selective for this type of yeast (Fungiqual A. Kandern. D E).

The result is shown in FIG. 21. It can be seen that skin surface treated with compounds according to the invention are suitable to significantly reduce the number/amount of the undesired microorganisms on skin. Skin reaction of the volunteer was confined to the area with seborrheic dermatitis, normal skin was not affected.

Example 35

Figure 1:
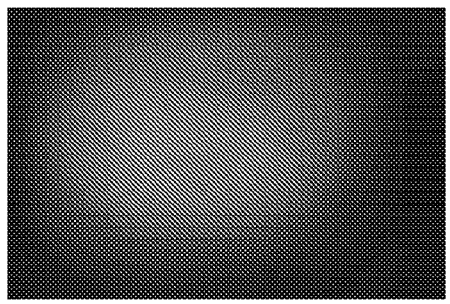
Figure 1B:
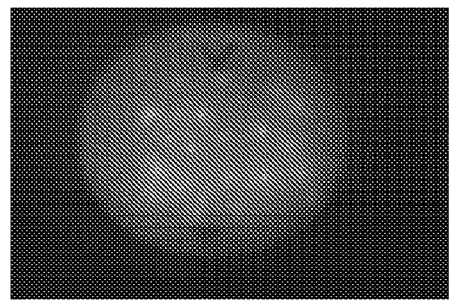
Figure 2:
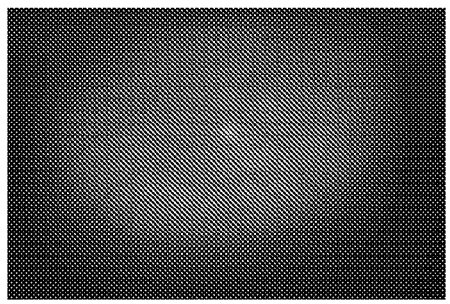
Figure 2B:
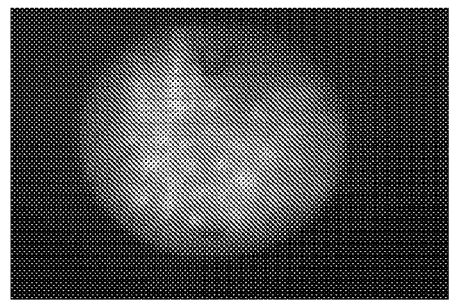
Figure 3:
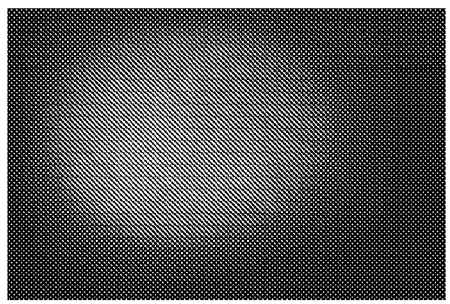
Figure 3:
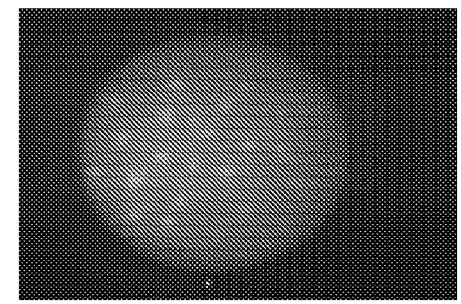
Figure 3:
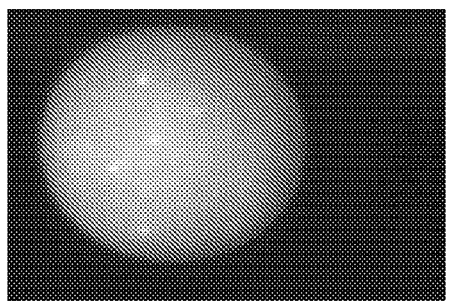
Figure 4:
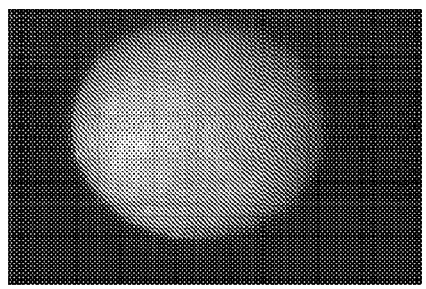
Figure 4:
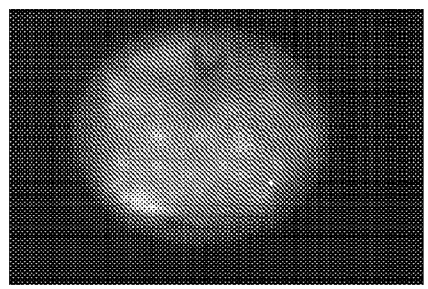
Figure 5:
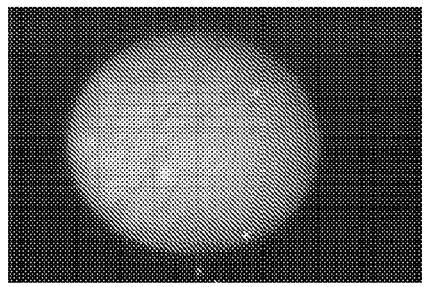
Figure 5:
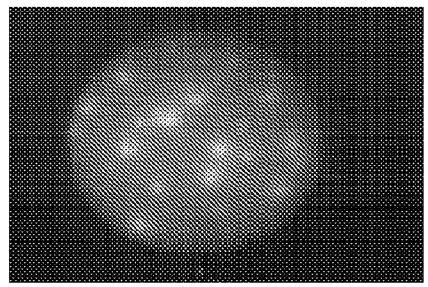
Figure 5:
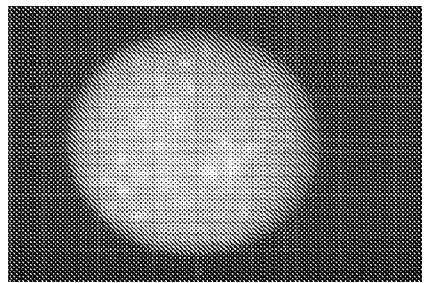
Figure 6:
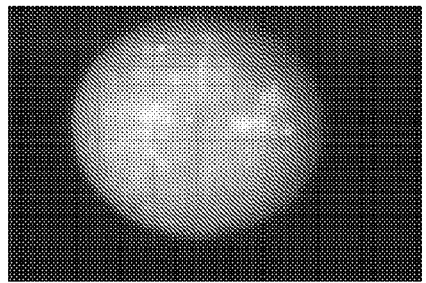
Figure 6:
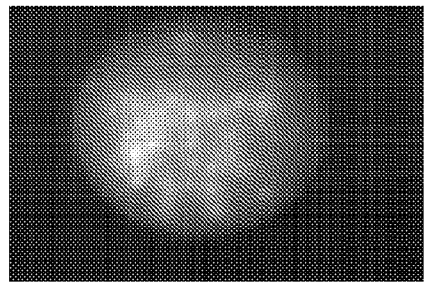
Figure 6:
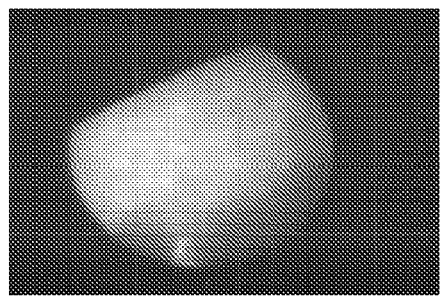
Figure 7:
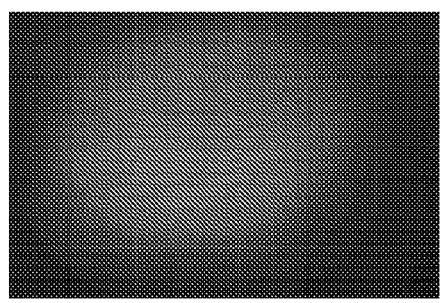
Figure 7:
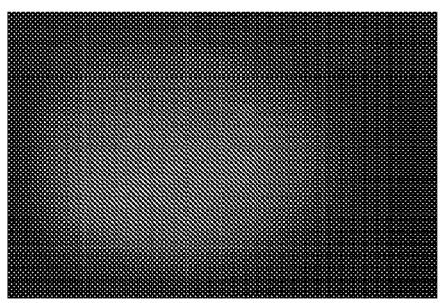
Figure 8:
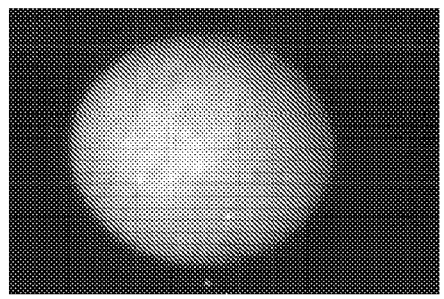
Figure 8:
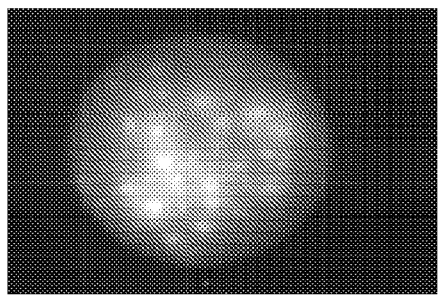
Figure 8:
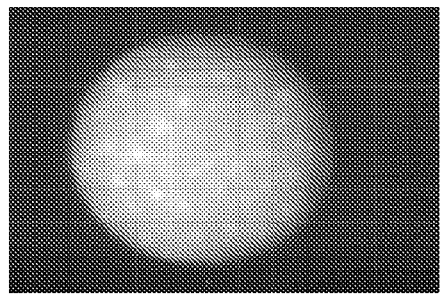
Figure 9:
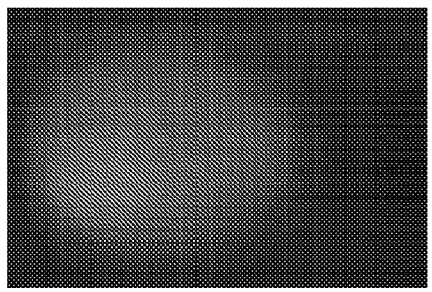
Figure 9:
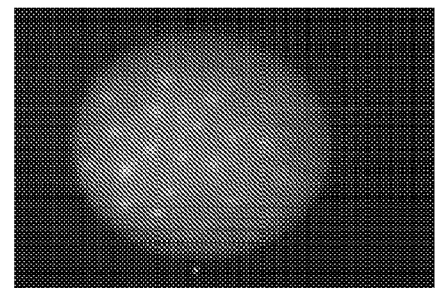
Figure 9:
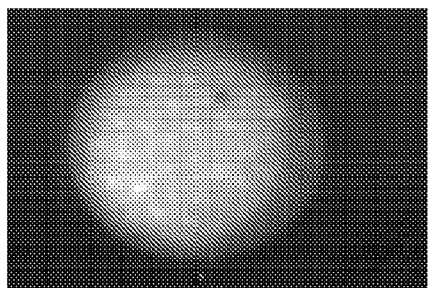
Figure 10:
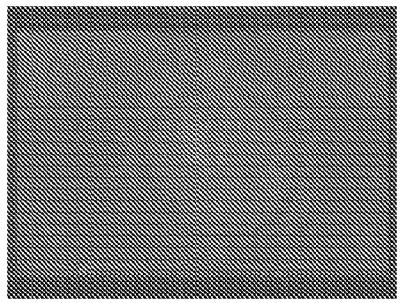
Figure 10:
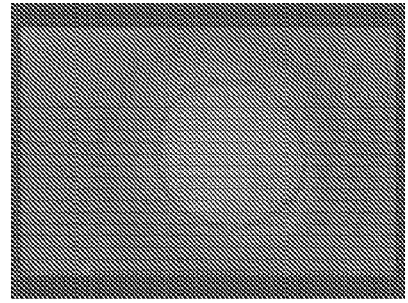
Figure 11:
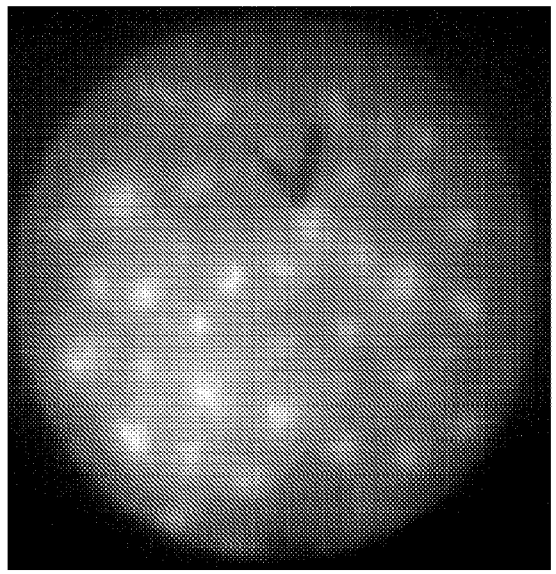
FIG. 11 shows a fluorescence photograph of skin to which a formulation comprising 20 wt. % of ALA-DGME, a compound of the present invention, was applied after epilation. It can be seen that fluorescence is discretely associated to specific small spots.
Figure 12:
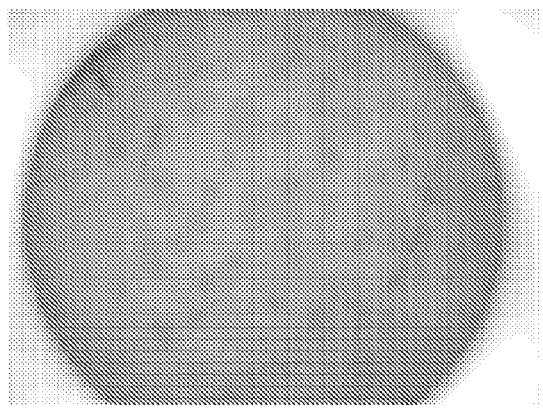
FIG. 12 is a normal photograph showing the same skin area as FIG. 11, showing the selective, limited skin reaction in form of redness around the hair follicles caused by the administration of the compounds of the present invention.
Figure 13:
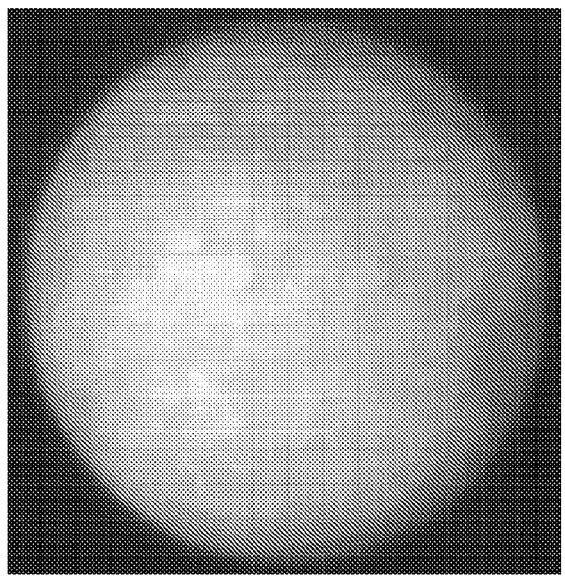
FIG. 13 is to be compared with FIG. 11 and shows a fluorescence photograph of skin to which a formulation comprising 20 wt. % of ALA, a compound of the prior art, was applied. It can be seen that fluorescence is non-specific and uniformly distributed over the entire skin area.
Figure 14:
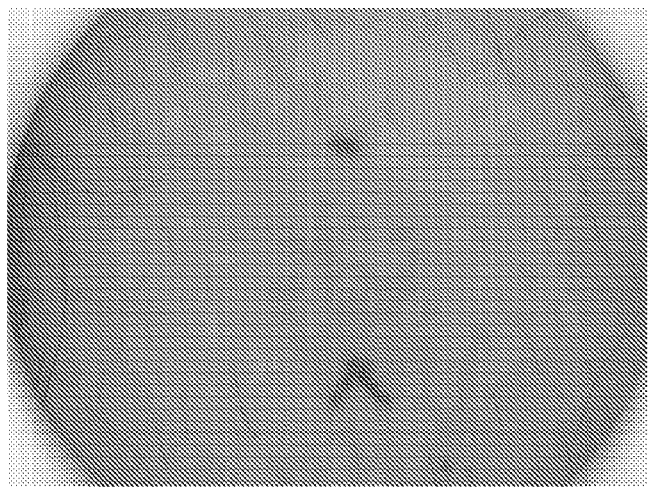
FIG. 14 is to be compared with FIG. 12 and is a normal photograph showing the same skin area as FIG. 13, showing non-selective, undesired skin reaction brought about by the administration of the compounds of the prior art.
Figure 15:
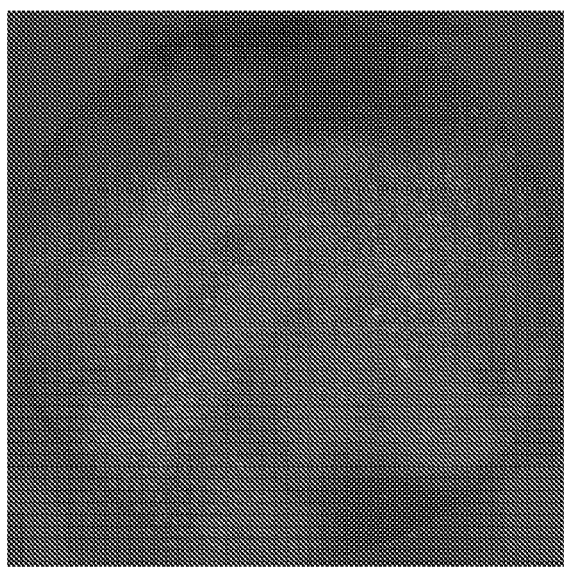
FIG. 15 is a fluorescence photograph of skin exhibiting seborrheic dermatitis onto which a compound of the present invention, ALA-DGME was topically applied. The selectiveness of the compound can be seen, as only affected skin area shows red fluorescence and healthy skin does not show fluorescence.
Figure 16:
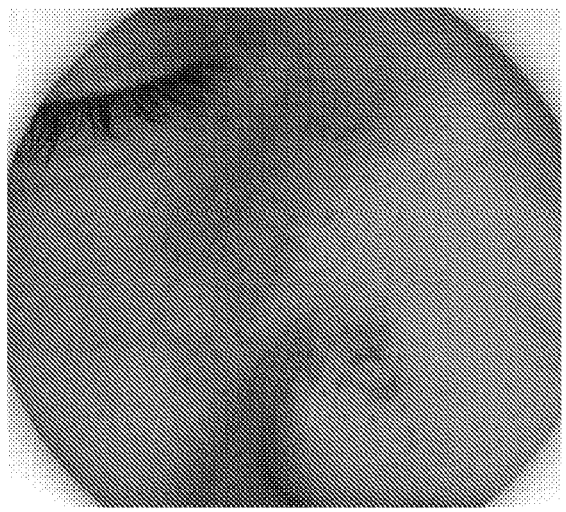
FIG. 16 is a normal photograph of the same skin area of FIG. 15, one day after PDT treatment. The skin reaction is confined to the zone of porphyrin fluorescence in FIG. 15.

Cosmetic Treatment of Seborrheic Dermatitis with the Compounds of the Present Invention ALA-DGME 5% is prepared in Cold cream as in the previous example. 15 mg of 5% ALA-DGME in Cold cream or placebo (Cold cream) are applied to the nose of a volunteer suffering from seborrheic dermatitis. 3 hours later, the zone, which received ALA-DGME or placebo is exposed to 5-15 J/cm$^2$ of red light. The result is shown in FIGS. 15 and 16. The treatment is the same as in Example 34. In FIG. 15, the photosensitizer has accumulated specifically in the skin area affected with SD as indicated by the red fluorescence. In FIG. 16, 24 hours after the PDT treatment, a slight redness, indicating a PDT effect, can be seen which is circumscribed to the area of skin affected with seborrheic dermatitis with no side effects to the surrounding skin.

Example 36

Cosmetic Treatment of Psoriasis Plaque with the Compounds of the Present Invention ALA-DGME 5% is prepared in Cold cream as in the previous example. 50 mg of 5% ALA-DGME in Cold cream are applied to the psoriatic plaque. 3 hours later, the zone which received ALA-DGME is exposed to 10-30 J/cm$^2$ of red light.

Figure 17:
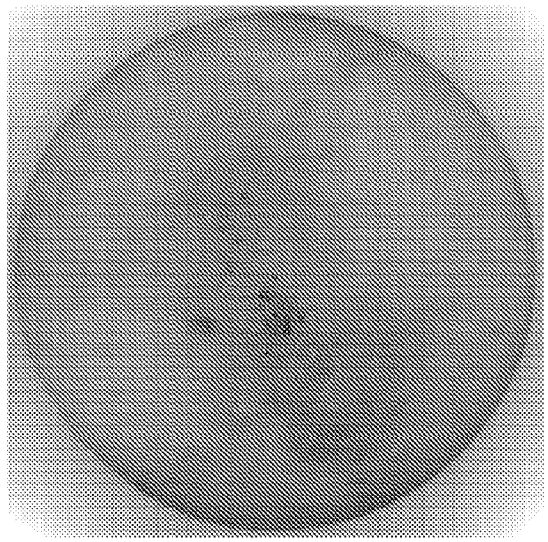
FIG. 17 is a normal photograph of a psoriasis plaque on the skin of an individual before treatment.
Figure 18:
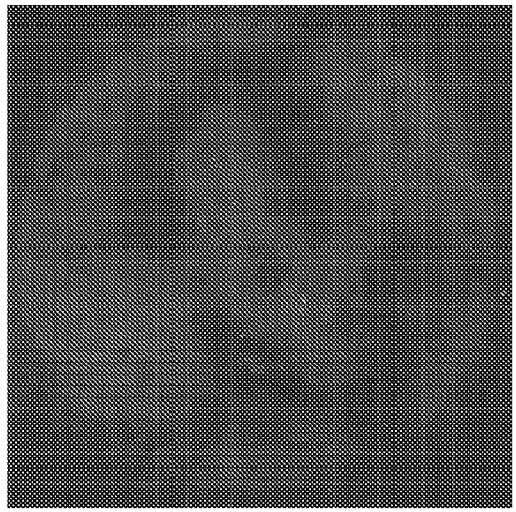
FIG. 18 is a fluorescence photograph of the skin of FIG. 17, onto which a formulation comprising 20 wt. % ALA-DGME was topically applied. The selectiveness of ALA-DGME can be recognized by the red fluorescence covering the psoriasis plaque solely.
Figure 19:
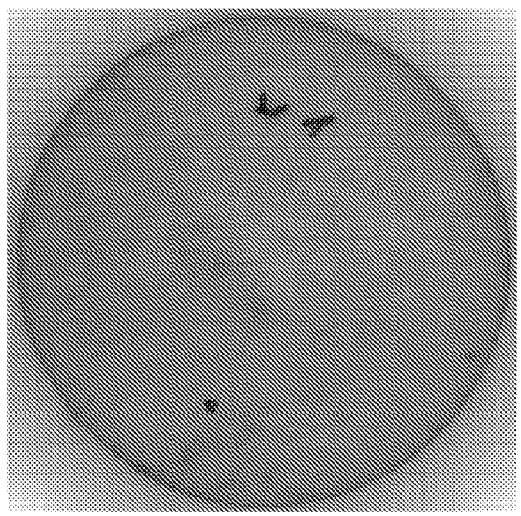
FIG. 19 is a normal photograph showing the same skin area as FIGS. 17 and 18, one month after weekly treatment of a psoriasis plaque. Comparison with FIG. 17 shows clear improvement.

The treatment is repeated 6 times with a 2 weeks interval. The result is shown in FIGS. 17, 18 and 19. The treatment is the same as in Example 34. The psoriatic plaque before the PDT treatment is shown in FIG. 17. In FIG. 18, the photosensitizer has accumulated specifically in the psoriasis lesions as indicated by the red fluorescence. FIG. 19 shows the plaque after several PDT treatments, which indicates partial clearance with no side effects to the surrounding skin.

Example 37

Method for Determining the Allergenic Potential of a Substance

The substance is prepared at a concentration of 60% in a standard "cold cream" excipient. Thirty-three (33) volunteers should be recruited. The cream is applied on the dorsal skin of the volunteers using 19 mm Hill Top Chambers® (Hill Top Research, Cincinnati, Ohio, USA) fulfilled with the formulation. The same patch test containing only cold cream (with no active) is used as negative control. The patch is left for 48 hours in contact with skin and then removed. Immediately after removal and at days 2, 4, 8 and 10 after removal of the patch test, the skin in the zone of application is observed by a dermatologist. The presence or absence of typical features of allergy will be reported immediately or at any of days 2, 4, 8 or 10 after patch removal. Typical features of allergy are the presence of an atopic dermatitis eczema with papulation, erythma, oedema and eventually pruritus or blistering. Individuals which showed typical features of allergic reaction on the zone of administration of the cream will, one month after the first application, receive a new patch test application with the substance at a concentration of 60% in a standard "cold cream" excipient. The patch test is left for 3 hours in contact with dorsal skin. The skin in the zone of application is observed by a dermatologist immediately after the removal of the patch and at days 2, 4, 8 and 10 after removal of the patch. If signs of allergy are confirmed on an individual in the course of the second patch test, the respective individual is considered to be allergic against the test substance, or in other words, the tested substance is allergenic for this individual.

The substance is considered non-allergenic if typical features of allergy are observed immediately or at any of days 2, 4, 8 or 10 in not more than one of the 33 individuals (3% or less). Preferably, the substance is considered non-allergenic if less than 3% of the test persons show signs of allergy as detailed above and confirmed by a dermatologist.

According to a preferred embodiment, one hundred (100) volunteers are recruited. A substance is considered as an allergen or as allergenic if typical features of allergy are observed in not more than one of 100 individuals (1% or less). Preferably, the substance is considered non-allergenic if less than 1% of the test persons show signs of allergy as detailed above and confirmed by a dermatologist.

The invention claimed is:

1. A 5-aminolevulinic acid (ALA) derivative compound, wherein said derivative compound is selected from any of the compounds of formulae (1), (2), (3), (6) or (12):

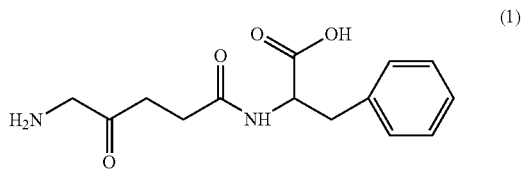

(1)

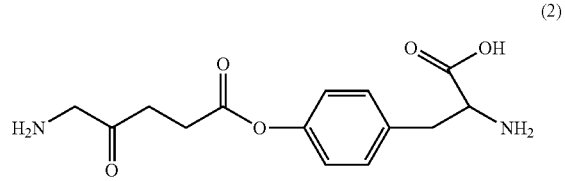

(2)

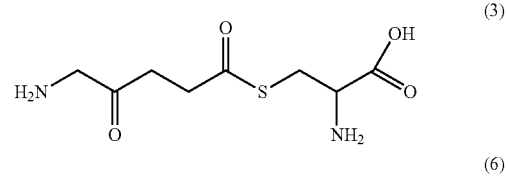

(3)

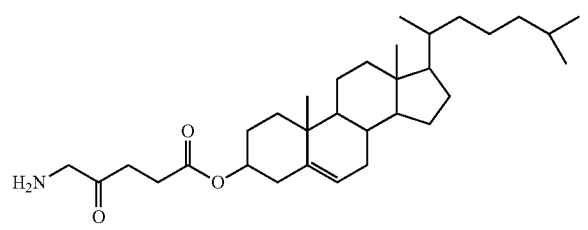

(6)

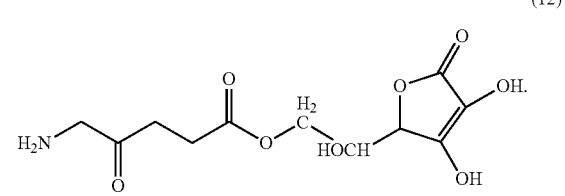

(12)

2. The 5-aminolevulinic acid (ALA) derivative compound of claim 1, wherein said derivative compound is a photosensitizer or a photosensitizer precursor and wherein said derivative compound has the property of being substantially incapable of passing through intact stratum corneum of an individual.

3. The 5-aminolevulinic acid (ALA) derivative compound of claim 1, wherein said derivative compound is non-allergenic.

4. A pharmaceutical composition comprising the 5-aminolevulinic acid (ALA) derivative compound of claim 1.

5. A cosmetic composition comprising the 5-aminolevulinic acid (ALA) derivative compound of claim 1.

* * * * *